United States Patent
Ushiyama

(10) Patent No.: US 12,264,136 B2
(45) Date of Patent: Apr. 1, 2025

(54) PRODUCTION METHOD FOR HEMIAMINAL COMPOUND AND PRODUCTION METHOD FOR HETEROCYCLIC COMPOUND

(71) Applicant: FUJIFILM Corporation, Tokyo (JP)

(72) Inventor: Aina Ushiyama, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 837 days.

(21) Appl. No.: 17/480,822

(22) Filed: Sep. 21, 2021

(65) Prior Publication Data

US 2022/0002257 A1 Jan. 6, 2022

Related U.S. Application Data

(63) Continuation of application No. PCT/JP2020/008655, filed on Mar. 2, 2020.

(30) Foreign Application Priority Data

Mar. 28, 2019 (JP) .................. 2019-064409

(51) Int. Cl.
*C07D 265/06* (2006.01)
*C07C 231/12* (2006.01)

(52) U.S. Cl.
CPC .......... *C07D 265/06* (2013.01); *C07C 231/12* (2013.01)

(58) Field of Classification Search
CPC .... C07D 265/06; C07C 231/12; C07C 231/08
USPC ......................................................... 544/97
See application file for complete search history.

(56) References Cited

U.S. PATENT DOCUMENTS

2009/0030173 A1 1/2009 Narizuka et al.
2018/0050976 A1 2/2018 Ishii et al.

FOREIGN PATENT DOCUMENTS

| JP | 6-009497 A | 1/1994 |
|---|---|---|
| JP | 2009-041002 A | 2/2009 |
| WO | 2016/132805 A1 | 8/2016 |

OTHER PUBLICATIONS

International Preliminary Report on Patentability dated Sep. 28, 2021 in International Application No. PCT/JP2020/008655.
Written Opinion of the International Searching Authority dated May 26, 2020 in International Application No. PCT/JP2020/008655.
International Search Report dated May 26, 2020 in International Application No. PCT/JP2020/008655.
Figueroa, R. et al., "Methyltrifluoropyruvate, e-EROS Encyclopedia of Reagents for Organic Synthesis", John Wiley & Sons, Ltd., 2007, pp. 1-13 (13 pages total).
Haruyasu Asahara et al., "Direct Synthesis of N-Acyl-N, O-hemiacetals via Nucleophilic Addition of Unactivated Amides and Their O-Acetylation: Access to α, α-Difunctionalized N-Acylimines", Advanced Synthesis & Catalysis, 2016, vol. 358, pp. 2817-2828 (12 pages total).
Stuart Lang et al., "Tandem oxidation-Wittig-Wittig sequences for the preparation of functionalised dienoates", Tetrahedron Letters, 2006, vol. 47, pp. 5489-5492 (4 pages total).
Tamejiro Hiyama, "The latest methods in organic synthesis—Design and strategy", Modern Organic Synthesis: An Introduction, Section "TEMPO", 2009, pp. 100-101 ( 1 page total).

*Primary Examiner* — Taylor V Oh
(74) *Attorney, Agent, or Firm* — Sughrue Mion, PLLC

(57) ABSTRACT

In a production method for a hemiaminal compound, a compound represented by Formula (1), a compound represented by Formula (2), and an oxidizing agent are mixed. A hemiaminal compound represented by Formula (3) is obtained. In a production method for a heterocyclic compound, a hemiaminal compound is mixed with a base.

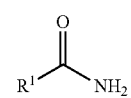

(1)

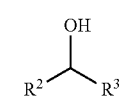

(2)

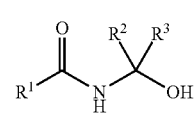

(3)

18 Claims, No Drawings

PRODUCTION METHOD FOR HEMIAMINAL COMPOUND AND PRODUCTION METHOD FOR HETEROCYCLIC COMPOUND

CROSS-REFERENCE TO RELATED APPLICATIONS

This application is a Continuation of PCT International Application No. PCT/JP2020/008655, filed on Mar. 2, 2020, which claims priority under 35 U.S.C. § 119(a) to Japanese Patent Application No. 2019-064409, filed on Mar. 28, 2019. Each of the above application(s) is hereby expressly incorporated by reference, in its entirety, into the present application.

BACKGROUND OF THE INVENTION

1. Field of the Invention

The present invention relates to a production method for a hemiaminal compound and a production method for a heterocyclic compound.

2. Description of the Related Art

A ketone having an electron withdrawing group, such as hexafluoroacetone, is used for various intended purposes.

For example, in JP2009-041002A, hexafluoroacetone is used as a raw material for synthesizing a compound having a hydroxyl group.

SUMMARY OF THE INVENTION

On the other hand, in the related art, there has been a demand for a method with which a hemiaminal compound can be easily produced. The hemiaminal compound means a compound having a structure in which an amino group is also bonded to a carbon to which a hydroxyl group is bonded.

The inventors of the present invention attempted to produce a hemiaminal compound using a ketone having an electron withdrawing group. However, since the ketone having an electron withdrawing group has high reactivity, it easily reacts with water to become an inactive diol compound, and thus is inferior in operability in the first place.

An object of the present invention is to provide a novel production method for a hemiaminal compound in consideration of the above circumstances.

Another object of the present invention is to provide a production method for a heterocyclic compound.

The inventors of the present invention have carried out intensive research to achieve the objects, and as a result, have found that the above-described objects can be achieved by the following configurations.

(1) A production method for a hemiaminal compound, comprising:
mixing a compound represented by Formula (1), a compound represented by Formula (2), and an oxidizing agent to obtain a hemiaminal compound represented by Formula (3).

(2) The production method according to (1), in which $R^2$ and $R^3$ each independently represent a fluorinated alkyl group having 1 to 10 carbon atoms.

(3) The production method according to (1) or (2), in which the mixing is carried out in a presence of a halogen-based solvent.

(4) The production method according to any one of (1) to (3), in which $R^1$ represents a hydrocarbon group having a leaving group.

(5) The production method according to (4), in which the leaving group is a halogen atom.

(6) The production method according to any one of (1) to (5), in which the oxidizing agent is selected from the group consisting of an organic nitroxyl radical, an N-hydroxyl form of an organic nitroxyl radical, and salts containing oxoammonium cations of an organic nitroxyl radical and the N-hydroxyl form of an organic nitroxyl radical.

(7) The production method according to any one of (1) to (6), in which the oxidizing agent is selected from the group consisting of a compound represented by Formula (4), a compound represented by Formula (5), and a compound represented by Formula (6).

(8) The production method according to (7), in which a reoxidizing agent is further used at the time of mixing.

(9) The production method according to (8), in which the reoxidizing agent includes a hypervalent iodine compound or an azodicarboxylic acid diester compound.

(10) The production method according to (8) or (9), in which the reoxidizing agent includes a hypervalent iodine compound.

(11) The production method according to any one of (1) to (10), in which the compound represented by Formula (1) is a compound represented by Formula (7), and
the hemiaminal compound represented by Formula (3) is a hemiaminal compound represented by Formula (8).

(12) A production method for a heterocyclic compound, comprising mixing the hemiaminal compound represented by Formula (8) obtained by the production method according to (11) with a base to obtain a heterocyclic compound represented by Formula (9).

According to the present invention, it is possible to provide a novel production method for a hemiaminal compound.

Further, according to the present invention, it is also possible to provide a production method for a heterocyclic compound.

DESCRIPTION OF THE PREFERRED EMBODIMENTS

In the following description, the present invention will be described in more detail. A numerical value range represented using "to" in the present specification means a range including the numerical values described before and after "to" as the lower limit and the upper limit respectively.

<Production Method for Hemiaminal Compound>

A production method for a hemiaminal compound according to the embodiment of the present invention (hereinafter, also referred to as a "present production method 1") is a method of mixing a compound represented by Formula (1), a compound represented by Formula (2), and an oxidizing agent to obtain a hemiaminal compound represented by Formula (3).

In the following, first, materials that are used in the present production method 1 will be described in detail, and then the procedure of the present production method 1 will be described in detail.

(Compound Represented by Formula (1))

In the present production method 1, a compound represented by Formula (1) (hereinafter, also referred to as a "compound 1") is used as a raw material.

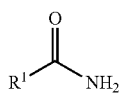

(1)

R¹ represents a hydrocarbon group which may have a substituent. The hydrocarbon group which may have a substituent is a monovalent group.

Examples of the hydrocarbon group in the hydrocarbon group which may have a substituent include an aliphatic hydrocarbon group, an aromatic hydrocarbon group, and a group in which these groups are combined.

The aliphatic hydrocarbon group may be linear, may be branched, or may have a cyclic structure. Examples of the aliphatic hydrocarbon group include an alkyl group, an alkenyl group, and an alkynyl group.

The aromatic hydrocarbon group may have a monocyclic structure or a polycyclic structure (a fused-ring structure). Examples of the aromatic hydrocarbon group include a phenyl group and a naphthalene group.

The number of carbon atoms in the hydrocarbon group is not particularly limited; however, the hydrocarbon group preferably has 1 to 30 carbon atoms, more preferably 1 to 10 carbon atoms, and still more preferably 2 to 6, since the yield of the hemiaminal compound is more excellent (hereinafter, also simply referred to as "the effect of the present invention is more excellent").

The kind of substituent which the hydrocarbon group may have is not particularly limited; however, examples thereof include a group selected from the substituent group W described later. The number of substituents is not particularly limited and may be one or plural. In the case of being plural, the number thereof is preferably 2 to 5, more preferably 2 or 3, and still more preferably 2.

The substituent group W: a halogen atom (a fluorine atom, a chlorine atom, a bromine atom, or an iodine atom), a heteroaryl group, a cyano group, a hydroxyl group, a carboxyl group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including anilino group), an ammonio group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, an alkyl or arylsulfinyl group, an alkyl or arylsulfonyl group, a acyl group, an aryloxycarbonyl group, an alkoxycarbonyl group, a carbamoyl group, an aryl or heterocyclic azo group, an imide group, a phosphino group, a phosphinyl group, a phosphinyloxy group, a phosphinylamino group, a phosphono group, a silyl group, a hydrazino group, an ureido group, and a boronic acid group (—B(OH)₂).

Further, the groups exemplified in the substituent group W may be further substituted with the group exemplified in the substituent group W.

R¹ is preferably a hydrocarbon group having a leaving group from the viewpoint of facilitating the production of the heterocyclic compound represented by Formula (9) described later.

The suitable aspect of the hydrocarbon group in the hydrocarbon group having a leaving group is the same as the suitable aspect of the hydrocarbon group in the hydrocarbon group represented by R¹ described above, which may have a substituent.

As the leaving group, known leaving groups can be mentioned, and examples thereof include, a halogen atom, an alkylsulfonyloxy group which may have a substituent, an arylsulfonyloxy group which may have a substituent, an alkylsulfonyl group which may have a substituent, an arylsulfonyl group which may have a substituent, a methoxy group, an aryl ester group, and a nitro group.

Examples of the substituent which each of the above groups may have is the groups exemplified in the substituent group W.

Examples of the halogen atom include a fluorine atom, a chlorine atom, a bromine atom, and an iodine atom, and a chlorine atom, a bromine atom, or an iodine atom is preferable.

The alkylsulfonyloxy group which may have a substituent is preferably an alkylsulfonyloxy group having 1 to 4 carbon atoms, which may have a halogen atom, and more preferably a trifluoromethylsulfonyloxy group or a methylsulfonyloxy group.

The arylsulfonyloxy group which may have a substituent is preferably a phenylsulfonyloxy group which may have a substituent and more preferably a phenylsulfonyloxy group, a p-toluenesulfonyloxy group, a p-chlorophenylsulfonyloxy group, or an o-nitrophenylsulfonyloxy group.

The alkylsulfonyl group which may have a substituent is preferably an alkylsulfonyl group having 1 to 4 carbon atoms, which may have a halogen atom, and more preferably a trifluoromethylsulfonyl group or a methylsulfonyl group.

The arylsulfonyl group which may have a substituent is preferably a phenylsulfonyl group which may have a substituent and more preferably a phenylsulfonyl group, a p-toluenesulfonyl group, a p-chlorophenylsulfonyl group, or an o-nitrophenylsulfonyl group.

The leaving group is preferably a halogen atom, a triflate group, a mesylate group, a phenylsulfonyloxy group, a p-toluenesulfonyloxy group, or an o-nitrophenylsulfonyloxy group, more preferably a chlorine atom, a bromine atom, or an iodine atom, and still more preferably a bromine atom.

The number of leaving groups in the hydrocarbon group represented by R¹, which has a leaving group, is not particularly limited and may be one or plural. Among the above, the number thereof is preferably 2 or 3 and more preferably 2 from the viewpoint of facilitating the production of the heterocyclic compound represented by Formula (9) described later.

The hydrocarbon group represented by R¹, which has a leaving group, is preferably a group represented by Formula (A). * represents a bonding position.

(A)

X¹ and X² represent a leaving group. The definition of the leaving group is as described above.

L¹ represents a hydrocarbon group which may have a substituent. The hydrocarbon group represented by L¹, which may have a substituent, corresponds to a divalent group. Examples of the substituent include the groups exemplified in the above-described the substituent group W.

Examples of the hydrocarbon group in the hydrocarbon group which may have a substituent include an aliphatic hydrocarbon group, an aromatic hydrocarbon group, and a group in which these groups are combined.

The aliphatic hydrocarbon group may be linear, may be branched, or may have a cyclic structure. Examples of the aliphatic hydrocarbon group include an alkylene group, an alkenylene group, and an alkynylene group.

The aromatic hydrocarbon group may have a monocyclic structure or a polycyclic structure (a fused-ring structure). Examples of the aromatic hydrocarbon group include a phenylene group.

The number of carbon atoms in the hydrocarbon group is not particularly limited; however, the hydrocarbon group preferably has 1 to 10 carbon atoms, more preferably 1 to 5 carbon atoms, still more preferably 1 to 3, and particularly preferably 1 or 2, from the viewpoint of facilitating the production of the heterocyclic compound represented by Formula (9) described later.

$L^2$ represents a single bond or a hydrocarbon group which may have a heteroatom. The hydrocarbon group represented by $L^2$, which may have a heteroatom, corresponds to a divalent group.

The suitable aspect of the hydrocarbon group in the hydrocarbon group represented by $L^2$, which may have a heteroatom, is the same as the suitable aspect of the hydrocarbon group in the hydrocarbon group represented by $L^1$ described above, which may have a substituent.

The kind of the heteroatom is not particularly limited; however, examples thereof include an oxygen atom, a sulfur atom, and a nitrogen atom (for example, in the form of —NH—).

The group represented by Formula (A) is preferably a group represented by Formula (B). * represents a bonding position.

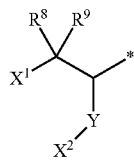

(B)

$R^8$ and $R^9$ each independently represent a hydrogen atom or a hydrocarbon group which may have a substituent.

Examples of the substituent of the hydrocarbon group which may have a substituent include the groups exemplified in the above-described substituent group W.

Examples of the hydrocarbon group in the hydrocarbon group represented by $R^8$ and $R^9$, which may have a substituent, include an aliphatic hydrocarbon group, an aromatic hydrocarbon group, and a group in which these groups are combined.

The aliphatic hydrocarbon group may be linear, may be branched, or may have a cyclic structure. Examples of the aliphatic hydrocarbon group include an alkyl group, an alkenyl group, and an alkynyl group.

The aromatic hydrocarbon group may have a monocyclic structure or a polycyclic structure (a fused-ring structure). Examples of the aromatic hydrocarbon group include a phenyl group.

The number of carbon atoms in the hydrocarbon group is not particularly limited; however, the hydrocarbon group preferably has 1 to 10 carbon atoms, more preferably 1 to 5 carbon atoms, still more preferably 1 to 3, and particularly preferably 1 or 2, from the viewpoint of facilitating the production of the heterocyclic compound represented by Formula (9) described later.

Y represents a single bond or an aliphatic hydrocarbon group having 1 to 5 carbon atoms, which may have a heteroatom.

The kind of the heteroatom is not particularly limited; however, examples thereof include an oxygen atom, a sulfur atom, and a nitrogen atom (for example, in the form of —NH—).

The aliphatic hydrocarbon group preferably has 1 to 3 carbon atoms, more preferably 1 or 2 carbon atoms, and still more preferably 1 carbon atom.

$X^1$ and $X^2$ each independently represent a leaving group. The definitions of $X^1$ and $X^2$ are as described above.

Examples of the compound 1 include the following compounds.

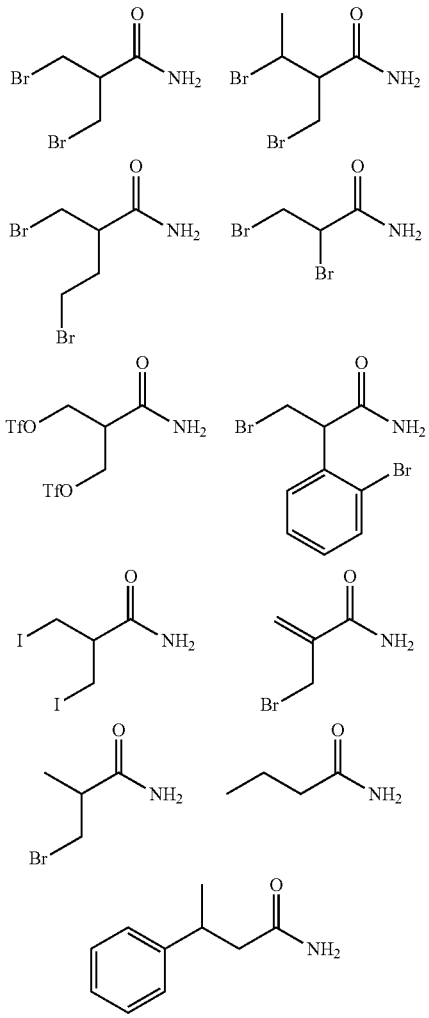

(Compound Represented by Formula (2))

In the present production method 1, a compound represented by Formula (2) (hereinafter, also referred to as a "compound 2") is used as a raw material.

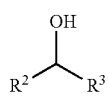

(2)

R² and R³ each independently represent a hydrogen atom or a substituent, where at least one of R² or R³ represents an electron withdrawing group. Among the above, it is preferable that both R² and R³ represent an electron withdrawing group since the effect of the present invention is more excellent.

The kind of the substituent represented by R² and R³ is not particularly limited, and examples thereof include an alkyl group which may have a substituent, an alkenyl group which may have a substituent, an alkynyl group which may have a substituent, an aryl group which may have a substituent, and the group exemplified in the above-described substituent group W.

Among them, the substituent represented by R² and R³ is preferably an electron withdrawing group.

The electron withdrawing group is a substituent having a Hammett's substituent constant σp value (a sigma para value) of 0.20 or more, and examples thereof include a hydrocarbon group substituted with a halogen atom, a cyano group, a nitro group, an acyl group, an alkyloxycarbonyl group, an aryloxycarbonyl group, an alkylsulfonyl group, an arylsulfonyl group, a dialkylsulfamoyl group, a dialkylamide group, and a heterocyclic group.

These electron withdrawing groups may be further substituted with a substituent.

Examples of the hydrocarbon group in the hydrocarbon group substituted with a halogen atom include an aliphatic hydrocarbon group, an aromatic hydrocarbon group, and a group in which these groups are combined. The aliphatic hydrocarbon group may be linear, may be branched, or may have a cyclic structure. Examples of the aliphatic hydrocarbon group include an alkyl group, an alkenyl group, and an alkynyl group.

The aromatic hydrocarbon group may have a monocyclic structure or a polycyclic structure (a fused-ring structure). Examples of the aromatic hydrocarbon group include a benzene ring group.

The number of carbon atoms in the hydrocarbon group substituted with a halogen atom is not particularly limited; however, the hydrocarbon group preferably has 1 to 15 carbon atoms, more preferably 1 to 6 carbon atoms, and still more preferably 1 to 4, from the viewpoint of facilitating the production of the heterocyclic compound represented by Formula (9) described later.

The number of halogen atoms in the hydrocarbon group substituted with a halogen atom is not particularly limited; however, the hydrocarbon group preferably has 1 to 10 halogen atoms, more preferably 1 to 8 halogen atoms, and still more preferably 1 to 5 halogen atoms since the effect of the present invention is more excellent.

The hydrocarbon group substituted with a halogen atom may be further substituted with a substituent. Examples of the substituent include the groups exemplified in the above-described the substituent group W.

Examples of the halogen atom include a fluorine atom, a chlorine atom, a bromine atom, and an iodine atom, and a fluorine atom is preferable.

The hydrocarbon group substituted with a halogen atom is preferably a fluorinated alkyl group (an alkyl group substituted with a fluorine atom) having 1 to 10 carbon atoms, more preferably a fluorinated alkyl group having 1 to 6 carbon atoms, and still more preferably a fluorinated alkyl group having 1 to 4 carbon atoms, since the effect of the present invention is more excellent. The alkyl group may be linear or branched.

The number of fluorine atoms in the fluorinated alkyl group having 1 to 10 carbon atoms is not particularly limited; however, the fluorinated alkyl group preferably has 1 to 10 halogen atoms, more preferably 1 to 8 halogen atoms, and still more preferably 1 to 5 halogen atoms since the effect of the present invention is more excellent.

The alkyloxycarbonyl group is a group represented by $R^a$—O—CO—*. $R^a$ represents an alkyl group (preferably an alkyl group having 1 to 3 carbon atoms). * represents a bonding position.

The aryloxycarbonyl group is a group represented by $R^b$—O—CO—*. $R^b$ represents an aryl group (preferably a phenyl group). * represents a bonding position.

The alkylsulfonyl group is a group represented by $R^a$—SO$_2$—*. $R^a$ represents an alkyl group (preferably an alkyl group having 1 to 3 carbon atoms). * represents a bonding position.

The arylsulfonyl group is a group represented by $R^b$—SO$_2$—*. $R^b$ represents an aryl group (preferably a phenyl group). * represents a bonding position.

The dialkylsulfamoyl group is a group represented by $(R^a)_2$—N—SO$_2$—*. $R^a$ represents an alkyl group (preferably an alkyl group having 1 to 3 carbon atoms). * represents a bonding position.

The dialkylamide group is a group represented by $(R^a)_2$—N—CO—*. $R^a$ represents an alkyl group (preferably an alkyl group having 1 to 3 carbon atoms). * represents a bonding position.

The Hammett's substituent constant σ value will be described. The Hammett's rule is a rule of thumb proposed by L. P. Hammett in 1935 for quantitatively discussing the effect of a substituent on the reaction or equilibrium of a benzene derivative, the validity of which is widely accepted today. A substituent constant obtained by the Hammett's rule include a σp value and a σm value, and these values can be found in many general books in the related field. For example, "Lange's Handbook of Chemistry" edited by J. A. Dean, 12th Edition, 1979 (McGraw-Hill), "Journal of Japanese Chemistry" Special Edition, No. 122, pp. 96 to 103, 1979 (Nankodo Co., Ltd.), and Chem. Rev., 1991, Volume 91, pp. 165 to 195 are mentioned. In the present invention, each of the substituents is limited or described with the Hammett's substituent constant σp value; however, it goes without saying that the substituents are not limited to substituents having a σp value known in the document, which can be found in the above-described book in the related field and the substituents also include a substituent that would be included in the range of the substituents in a case where a σp value is measured based on Hammett's rule even in a case of being unknown in the document.

As described above, the electron withdrawing group is a substituent having a Hammett's substituent constant σp value of 0.20 or more, and the σp value is preferably 0.25 or more and more preferably 0.30 or more. The upper limit thereof is not particularly limited; however, it is preferably 0.80 or less.

Specific examples of the electron withdrawing group include a cyano group (0.66), a carboxyl group (—COOH: 0.45), an alkyloxycycarbonyl group (—COOMe: 0.45), an aryloxycarbonyl group (—COOPh: 0.44), a carbamoyl group (—CONH$_2$: 0.36), an alkylcarbonyl group (—COMe:

0.50), an arylcarbonyl group (—COPh: 0.43), an alkylsulfonyl group (—SO$_2$Me: 0.72), and an arylsulfonyl group (—SO$_2$Ph: 0.68).

In the present specification, Me represents a methyl group, and Ph represents a phenyl group. The values in parentheses are σp values of the representative substituents selected from Chem. Rev., 1991, Volume 91, pp. 165 to 195.

Examples of the compound 2 include the following compounds.

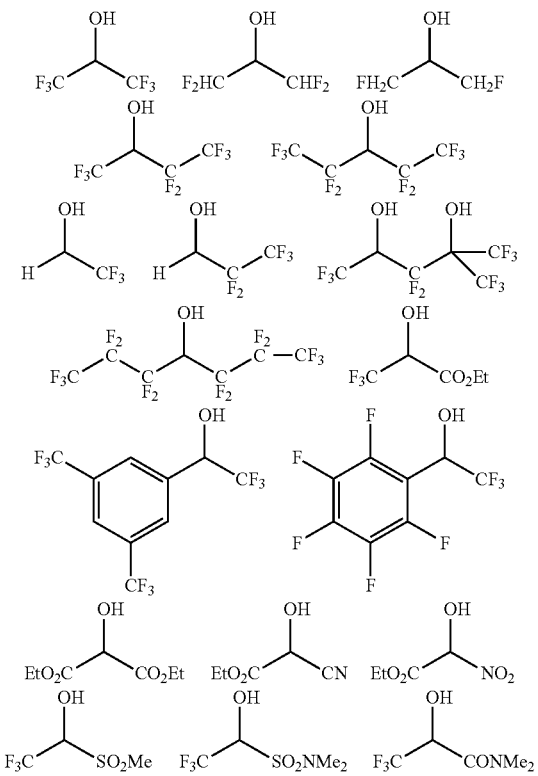

(Oxidizing Agent)

In the present production method 1, an oxidizing agent is used. The oxidizing agent plays a role in oxidizing the compound 2 in the reaction system. That is, the compound 2 is oxidized by the oxidizing agent, whereby a ketone compound is generated in the reaction system. A compound represented by Formula (3) described later is generated by reacting an amide group in the compound 1 with the ketone compound generated in the system.

The kind of the oxidizing agent is not particularly limited, and examples of the oxidizing agent include known oxidizing agents. Examples thereof include an organic nitroxyl radical, an N-hydroxyl form of an organic nitroxyl radical, and salts containing oxoammonium cations of an organic nitroxyl radical and the N-hydroxyl form of an organic nitroxyl radical. In addition to the above, examples thereof include peroxy acid, hydrogen peroxide, a hypohalous acid or a salt thereof, perhalogenate or a salt thereof, a persulfate, a halogenating agent (for example, N-bromosuccinimide), trihalogenated isocyanuric acids, diacetoxyiodoarenes, oxygen, and a mixture thereof.

The oxidizing agent is preferably a compound represented by Formula (4) (hereinafter, also referred to as a "compound 4"), a compound represented by Formula (5) (hereinafter, also referred to as a "compound 5"), or a compound represented by Formula (6) (hereinafter, also referred to as a "compound 6"). Hereinafter, the compound 4 to the compound 6 are collectively referred to as "nitroxyl radicals species".

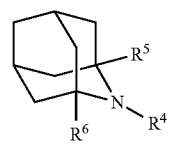

(4)

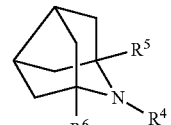

(5)

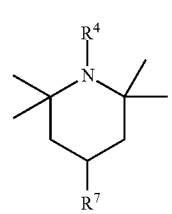

(6)

In Formula (4) to Formula (6), $R^4$ represents an oxyradical group or a hydroxyl group.

The oxyradical group is a group represented by *—O. * represents a bonding position.

In Formula (4) and Formula (5), $R^5$ and $R^6$ each independently represent a hydrogen atom or a methyl group.

In Formula (6), $R^7$ represents a hydrogen atom, a halogen atom, a hydroxyl group, an acyloxy group, an alkoxy group, an alkoxycarbonyl group, an amino group, an oxo group, a sulfonyloxy group, an N-alkylcarbamoyloxy group, a carboxyl group, a cyano group, an isocyanato group, or an isothiocyanato group.

Examples of the halogen atom include a fluorine atom, a chlorine atom, a bromine atom, and an iodine atom, and a fluorine atom, a chlorine atom, or a bromine atom is preferable.

The alkoxy group is represented by —OR$^c$, where R$^c$ represents a hydrocarbon group. The hydrocarbon group is preferably an alkyl group having 1 to 12 carbon atoms, an alkenyl group having 2 to 12 carbon atoms, an alkynyl group having 2 to 12 carbon atoms, or an aryl group having 6 to 20 carbon atoms, and more preferably a methyl group. In R$^c$, a part of hydrogen atoms may be substituted with a halogen atom.

The acyloxy group is represented by —O—CO—R$^d$, where R$^d$ represents a hydrogen atom, an alkyl group having 1 to 12 carbon atoms, an alkenyl group having 1 to 12 carbon atoms, or an aryl group having 6 to 20 carbon atoms.

The acylamino group is represented by —NH—CO—R$^e$, where R$^e$ represents a hydrogen atom, an alkyl group having 1 to 12 carbon atoms, or an aryl group having 6 to 20 carbon atoms.

The sulfonyloxy group is represented by —O—SO$_2$—R$^f$, where R$^f$ represents an alkyl group having 1 to 12 carbon atoms or an aryl group having 6 to 20 carbon atoms.

Examples of the nitroxyl radicals species include 2,2,6,6-tetramethylpiperidin-1-oxyl (TEMPO), 4-hydroxyl TEMPO, 4-amino-TEMPO, 4-methoxy-TEMPO, 4-ethoxy-TEMPO, 4-phenoxy-TEMPO, 4-acetoxy-TEMPO, 4-benzoyloxy-TEMPO, 4-methacrylate-TEMPO, 4-acetamide-TEMPO, 4-methylsulfonyloxy-TEMPO, 4-paratoluenesulfonyloxy-TEMPO, 4-oxo-TEMPO, 2-azaadamantan-N-hydroxyl, 2-azaadamantan-N-oxyl, 1-methyl-2-azaadamantan-N-oxyl, 9-azanoradamantan-N-oxyl (hereinafter, also referred to as "nor-AZADO"), and 1,5-dimethyl-9-azanoradamantan-N-oxyl.

(Compound Represented by Formula (3))

In the present production method 1, the compound (hereinafter, also referred to as the "compound 3") represented by Formula (3) is obtained.

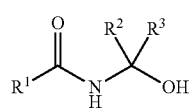

(3)

The definitions of $R^1$ to $R^3$ are as described above.

(Other Components)

In the present production method 1, components other than the above-described components may be used.

For example, in the present production method 1, a reoxidizing agent may be further used. That is, the compound represented by Formula (1), the compound represented by Formula (2), an oxidizing agent, and a reoxidizing agent can be mixed to obtain the hemiaminal compound represented by Formula (3). More preferably, the compound 1, the compound 2, an oxidizing agent selected from the group consisting of the compound represented by Formula (4), the compound represented by Formula (5), and the compound represented by Formula (6), and a reoxidizing agent may be mixed to obtain the compound 3.

The reoxidizing agent (the co-oxidizing agent) can be appropriately selected from those that are generally used in the oxidation reaction using nitroxyl radicals species. Examples of the reoxidizing agent include peroxy acid, hydrogen peroxide, an organic peroxide (for example, metachloroperbenzoic acid), a hypohalous acid or a salt thereof, perhalogenate or a salt thereof, a persulfate, a halogenating agent (for example, N-bromosuccinimide), chlorine, bromine, trihalogenated isocyanuric acids, diacetoxyiodoarenes, an azodicarboxylic acid diester compound, oxygen, a monovalent or divalent copper chloride, and a mixture thereof.

More specific examples thereof include iodobenzene diacetate, diethyl azodicarboxylate, 4-methylmorpholine N-oxide, trichloroisocyanuric acid, and N-chlorosuccinimide.

The reoxidizing agent is preferably a hypervalent iodine compound or an azodicarboxylic acid diester compound.

The hypervalent iodine compound is a compound containing a hypervalent iodine. More specifically, it is a compound containing iodine having more than eight electrons in the valence shell. Examples of the hypervalent iodine compound include 1-acetoxy-5-bromo-1,2-benziodoxysol-3-(1H)-one, [bis(trifluoroacetoxy)iodo]benzene, [bis(trifluoroacetoxy) iodo]pentafluorobenzene, 1-(tert-butylperoxy)-1,2-benziodoxysol-3-(1H)-one, bis(pyridine) iodonium tetrafluoroborate, Dess-Martin periodinane, iodosobenzene, 2-iodosobenzoic acid, iodobenzene diacetate, 2-iodoxybenzoic acid, and [hydroxyl(tosyloxy)iodo] benzene.

Examples of the azodicarboxylic acid diester compound include dimethyl azodicarboxylate, diethyl azodicarboxylate, diisopropyl azodicarboxylate, di-tert-butyl azodicarboxylate, dibenzyl azodicarboxylate, and bis(2-methoxyethyl) azodicarboxylate.

In the present production method 1, the above mixing may be carried out in the presence of a solvent.

The kind of the solvent used is not particularly limited, and examples of the solvent include an organic solvent. Examples of the organic solvent include a halogen-based solvent (for example, dichloromethane, tetrachloroethane, or chloroform), an amide-based solvent (for example, N,N-dimethylformamide), a sulfoxide-based solvent (for example, dimethylsulfoxide), a heterocyclic compound (for example, pyridine), a hydrocarbon-based solvent (for example, benzene or hexane), an ester-based solvent (for example, methyl acetate, ethyl acetate, or butyl acetate), a ketone-based solvent (for example, acetone or methyl ethyl ketone), a nitrile-based solvent (for example, acetonitrile), and an ether-based solvent (for example, tetrahydrofuran or 1,2-dimethoxyethane). Among them, a halogen-based solvent or a hydrocarbon-based solvent is preferable, and a halogen-based solvent is more preferable since the effect of the present invention is more excellent.

The halogen-based solvent is a solvent containing a halogen atom and is preferably a hydrocarbon containing a halogen atom. That is, it is preferably a hydrocarbon in which a part of hydrogen atoms are substituted with a halogen atom. The halogen-based solvent preferably has 1 to 3 carbon atoms and more preferably 1 or 2 carbon atoms. The halogen-based solvent preferably has 1 to 6 halogen atoms and more preferably 2 to 4 halogen atoms.

(Procedure of Present Production Method 1)

In the present production method 1, the procedure is not particularly limited as long as the compound 1, the compound 2, and the oxidizing agent can be mixed. For example, the compound 1, the compound 2, and an oxidizing agent may be mixed collectively, or two of the compound 1, the compound 2, and an oxidizing agent may be mixed first, and then the rest may be further added. Among the above, it is preferable that the compound 1 and the compound 2 are mixed, and then an oxidizing agent is further added and mixed, since the effect of the present invention is more excellent.

The ratio of the molar amount of the compound 1 to be used to the molar amount of the compound 2 to be used (the molar amount of the compound 1 to be used/the molar amount of the compound 2 to be used) is not particularly limited; however, it is preferably 0.1 to 10, more preferably 0.2 to 5, and still more preferably 0.25 to 1, since the effect of the present invention is more excellent.

The ratio of the molar amount of the oxidizing agent to be used to the molar amount of the compound 2 to be used (the molar amount of the oxidizing agent to be used/the molar amount of the compound 2 to be used) is not particularly limited; however, it is preferably 0.3 to 3 and more preferably 0.5 to 1.5 since the effect of the present invention is more excellent.

In a case where a reoxidizing agent is used, the ratio of the molar amount of the oxidizing agent to be used to the molar amount of the reoxidizing agent to be used (the molar amount of the oxidizing agent to be used/the molar amount of the reoxidizing agent to be used) is not particularly limited; however, it is preferably 0.001 to 0.5 and more preferably 0.01 to 0.1 since the effect of the present invention is more excellent.

The temperature condition at the time of mixing is not particularly limited; however, the temperature is preferably −80° C. to 80° C. and more preferably −20° C. to 30° C. since the effect of the present invention is more excellent.

The mixing time is not particularly limited; however, it is preferably 0.5 to 50 hours and more preferably 1 to 10 hours since the effect of the present invention is more excellent.

After completion of the reaction, as necessary, the obtained product may be subjected to a treatment for separating the compound 3, which is the target compound. The separation method is not particularly limited: however, examples thereof include known methods such as distillation and liquid separation extraction.

One of the suitable aspects of the present production method 1 is an aspect in which a compound represented by Formula (7) is used as the compound 1 to obtain a hemiaminal compound (hereinafter, also referred to as a "compound 8") represented by Formula (8) as the compound 3.

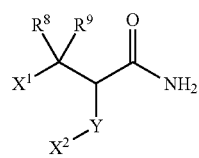

(7)

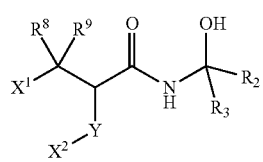

(8)

The definitions of $X^1$, $X^2$, $R^2$, $R^3$, $R^8$, $R^9$, and Y are as described above.

<Production Method for Heterocyclic Compound>

A production method for a heterocyclic compound according to the embodiment of the present invention (hereinafter, also referred to as a "present production method 2") is a method of mixing the compound 8 with a base to obtain a heterocyclic compound (hereinafter, also referred to as a "compound 9) represented by Formula (9) described later".

In the following, first, materials that are used in the present production method 1 will be described in detail, and then the procedure of the present production method 1 will be described in detail.

The definition of the compound 8 is as described above.

(Base)

In present production method 2, a base is used. In a case where the compound 8 is mixed with a base, the cyclization reaction and the double bond formation reaction proceed together with the elimination of the leaving group, and the desired compound 9 is obtained.

The kind of the base is not particularly limited, and a known base can be used. The base is preferably a nitrogen-containing basic compound. Examples of the nitrogen-containing basic compound include diazabicycloundecene (DBU), N,N-dimethyl-4-aminopyridine, N,N-diisopropylethylamine, tributylamine, triethylamine, and diazabicyclooctane.

(Compound Represented by Formula (9))

In the present production method 2, the compound 9 is obtained.

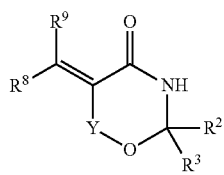

(9)

The definitions of $R^2$, $R^3$, $R^8$, $R^9$, and Y are as described above.

(Other Components)

In the present production method 2, components other than the above-described components may be used.

In the present production method 2, the above mixing may be carried out in the presence of a solvent. The kind of the solvent used is not particularly limited, and examples thereof include the solvents exemplified in the present production method 1.

(Procedure of Present Production Method 2)

In the present production method 2, the procedure is not particularly limited as long as the compound 8 and a base can be mixed. For example, the compound 8 and a base may be mixed collectively, or a base may be gradually added to the compound 8.

The ratio of the molar amount of the base to be used to the molar amount of the compound 8 to be used (the molar amount of the base to be used/the molar amount of the compound 8 to be used) is not particularly limited; however, it is preferably 0.1 to 10, more preferably 0.5 to 8, and still more preferably 1 to 4, since the effect of the present invention is more excellent.

The temperature condition at the time of mixing is not particularly limited; however, the temperature is preferably −80° C. to 50° C. and more preferably −20° C. to 30° C. since the effect of the present invention is more excellent.

The mixing time is not particularly limited; however, it is preferably 0.1 to 30 hours and more preferably 0.5 to 5 hours since the effect of the present invention is more excellent.

After completion of the reaction, as necessary, the obtained product may be subjected to a treatment for separating the compound 9, which is the target compound. The separation method is not particularly limited: however, examples thereof include known methods such as distillation and liquid separation extraction.

The compound 9 can be applied to various application uses.

For example, it can be used as a monomer in the production of a resin. More specifically, it can be used as a monomer in the production of a photosensitive resin and a monomer in the production of a resin for a semiconductor resist.

EXAMPLES

Hereinafter, the present invention will be described in more detail based on Examples; however, the present invention is not limited to these Examples.

Example 1

A mixed solution of 3-bromo-2-bromomethylpropanamide (5.02 g, 20.5 mmol), hexafluoroisopropanol (6.89 g, 41 mmol), and methylene chloride (50 ml) was cooled to 0° C., and iodobenzenediacetate (PhI(OAc)$_2$) (13.21 g, 41 mmol) and 2-hydroxyl-2-azaadamantane (0.31 g, 2.05 mmol) were added the mixed solution. Then, the obtained solution was heated to 20° C. and then stirred for 6 hours. A 10 mass % sodium sulfite aqueous solution (50 ml) was added to the obtained solution, and the mixture was subjected to liquid separation extraction to obtain a hemiaminal compound (yield: 90%).

Next, the obtained hemiaminal compound was dissolved in methylene chloride to obtain a solution, which subsequently cooled to 0° C., and diazabicycloundecene (DBU) (6.87 g, 45.1 mmol) was slowly added dropwise to the cooled solution.

The obtained solution was stirred at 0° C. for 30 minutes and then concentrated under reduced pressure. Then, 2 M KOH aqueous solution (50 ml) and heptane (50 ml) were added to the obtained solution, the organic phase was removed, and then 2 M HCl aqueous solution (50 ml) and methylene chloride (50 ml) were added to the remainder. Then, the water phase was removed, and the remaining organic phase was concentrated under reduced pressure to obtain a heterocyclic compound (yield: 81%).

It is noted that the Hammett's substituent constant σp value of the —CF$_3$ group in hexafluoroisopropanol is 0.54, where the —CF$_3$ group corresponds to an electron withdrawing group.

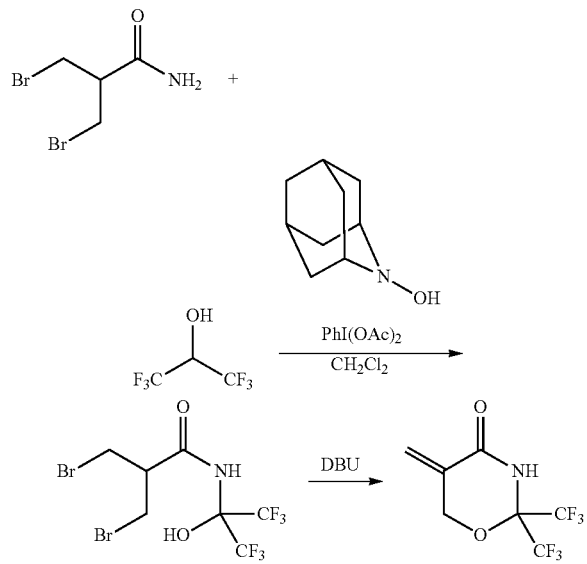

Examples 2 to 5

Hemiaminal compounds and heterocyclic compounds were obtained according to the same procedure as in Example 1 except that the kinds of oxidizing agents and reoxidizing agents used, the kinds of solvents, and the reaction temperatures were changed as indicated in Table 1.

"Yield" in Table 1 represents the yield of the hemiaminal compound.

In Table 1, "DIAD (AcOH)" represents a mixture of diisopropyl azodicarboxylate (DIAD) (4.97 g, 24.6 mmol) and acetic acid (AcOH) (1.23 g, 20.5 mmol).

In Table 1, "nor-AZADO" is the following compound.

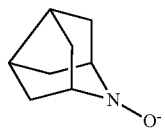

TABLE 1

| Example | Oxidizing agent/reoxidizing agent | Solvent | Reaction temperature | Yield |
|---|---|---|---|---|
| 1 | 2-hydroxyl-2-azaadamantane/ PhI(OAc)$_2$ | CH$_2$Cl$_2$ | 20° C. | 90% |
| 2 | 2-hydroxyl-2-azaadamantane/ PhI(OAc)$_2$ | C$_2$H$_2$Cl$_4$ | 20° C. | 88% |
| 3 | 2-hydroxyl-2-azaadamantane/ PhI(OAc)$_2$ | Toluene | 20° C. | 54% |
| 4 | 2-hydroxyl-2-azaadamantane/ DIAD (AcOH added) | CH$_2$Cl$_2$ | 20° C. | 70% |
| 5 | nor-AZADO/PhI(OAc)2 | CH$_2$Cl$_2$ | 20° C. | 91% |

As shown in Table 1, according to the present production method 1, the hemiaminal compound could be efficiently produced. In addition, the heterocyclic compound could be efficiently produced according to the present production method 2.

From the comparison between Examples 1 to 3, it has been confirmed that a more excellent effect can be obtained in a case where a halogen-based solvent is used as the solvent.

Further, from the comparison between Examples 1 and 4, it has been confirmed that a more excellent effect can be obtained in a case where a hypervalent iodine compound is used.

It has been confirmed that a predetermined hemiaminal compound is obtained as well in a case where the solvent of Example 1 is changed to acetonitrile. However, the yield is inferior to that of Example 1.

In addition, it has been confirmed that a predetermined hemiaminal compound is obtained as well in a case where the oxidizing agent of Example 1 is changed to TEMPO. However, the yield is inferior to that of Example 1.

In addition, it has been confirmed that a predetermined hemiaminal compound is obtained as well in a case where the oxidizing agent of Example 1 is changed to dimethylsulfoxide and the reaction temperature is set to −78° C. However, the yield is inferior to that of Example 1.

In addition, it has been confirmed that a predetermined hemiaminal compound is obtained as well in a case where, in Example, the oxidizing agent is changed to potassium peroxymonosulfate, the reoxidizing agent is changed to potassium 2-iodo-5-methylbenzenesulfonate, the solvent is changed to acetonitrile, and the reaction temperature is changed to 50° C. However, the yield is inferior to that of Example 1.

Example 6

A hemiaminal compound (yield: 83%) and a heterocyclic compound (yield: 81%) were obtained according to the same procedure as in Example 1 except that the raw materials used were changed to the compounds shown in the following scheme.

The Hammett's substituent constant σp value of a —CF$_2$C(OH)(CF$_3$)$_2$ group in the following raw material compound is 0.40 or more, where the —CF$_2$C(OH)(CF$_3$)$_2$ group corresponds to an electron withdrawing group.

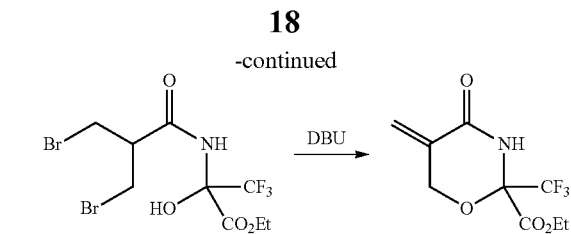

Hemiaminal-3

Example 8

A hemiaminal compound (yield: 90%) was obtained according to the same procedure as in Example 1 except that the raw materials used were changed to the compounds shown in the following scheme.

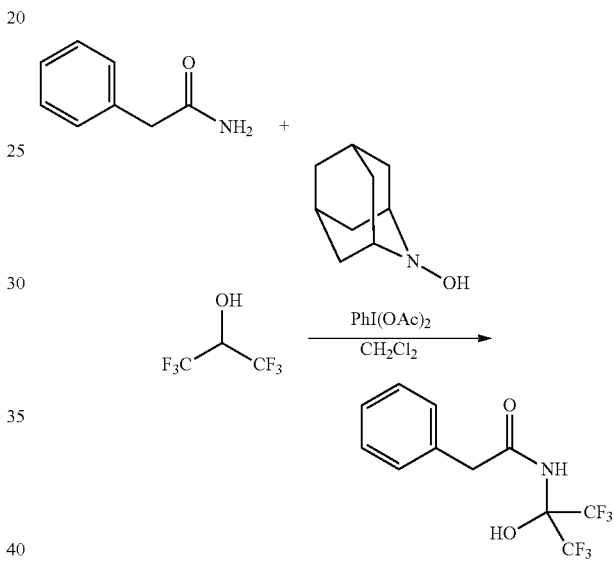

Example 9

A hemiaminal compound (yield: 50%) was obtained according to the same procedure as in Example 1 except that the raw materials used were changed to the compounds shown in the following scheme.

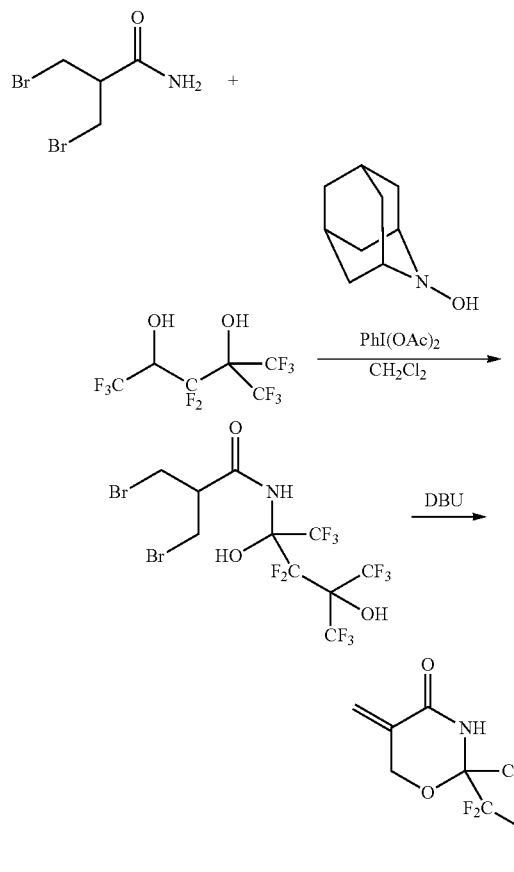

Example 7

A hemiaminal compound (yield: 70%) and a heterocyclic compound (yield: 63%) were obtained according to the same procedure as in Example 1 except that the raw materials used were changed to the compounds shown in the following scheme.

The Hammett's substituent constant σp value of a —CO₂Et group (Et: ethyl group) in the following raw material compound is 0.45, where the —CO₂Et group corresponds to the electron withdrawing group.

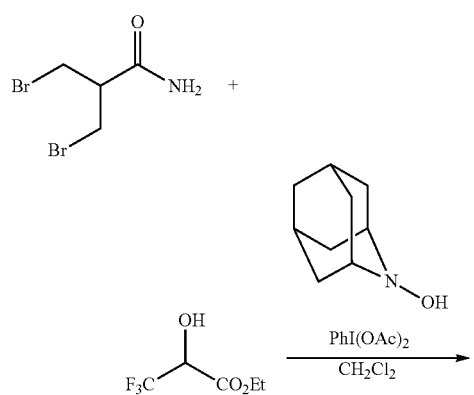

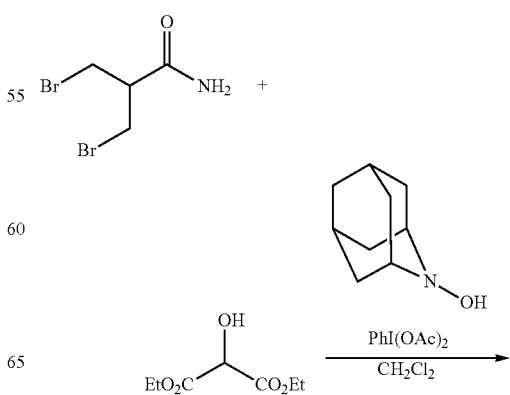

-continued

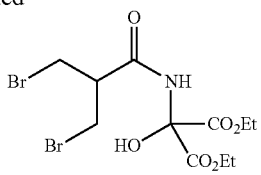

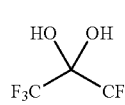 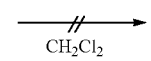 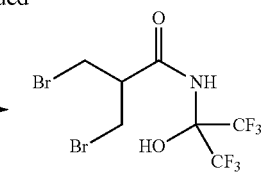

Example 10

A hemiaminal compound (yield: 91%) and a heterocyclic compound (yield: 84%) were obtained according to the same procedure as in Example 1 except that the raw materials used were changed to the compounds shown in the following scheme and the base was changed to N,N-diisopropylethylamine (3.18 g, 24.6 mmol).

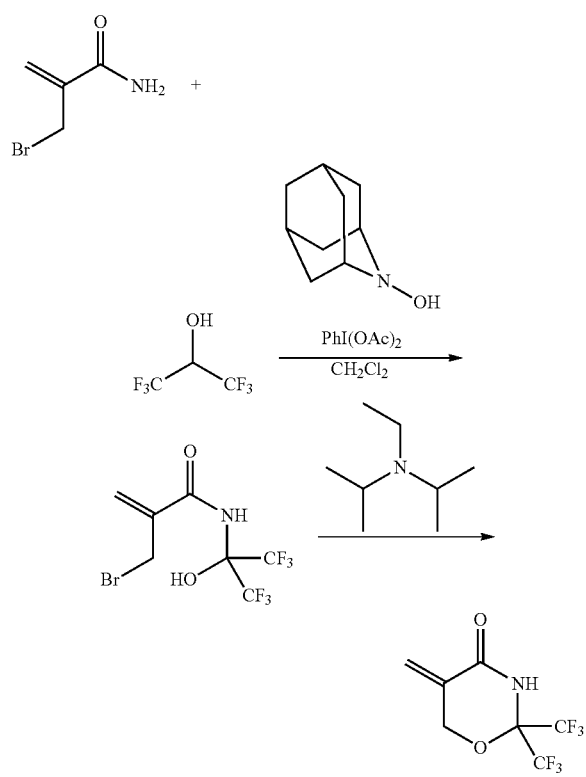

Comparative Example 1

A hexafluoroacetone hydrate (9.02 g, 41.0 mmol), which is a water adduct of 3-bromo-2-bromomethylpropanamide (5.02 g, 20.5 mmol), and hexafluoroacetone were added to methylene chloride (50 ml) and stirred at 20° C., but the reaction did not proceed.

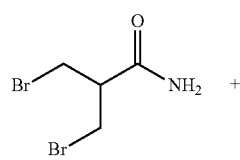

What is claimed is:

1. A production method for a hemiaminal compound, comprising:
mixing a compound represented by Formula (1), a compound represented by Formula (2), and an oxidizing agent to obtain a hemiaminal compound represented by Formula (3),

 (1)

 (2)

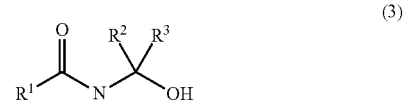 (3)

in the formulae, $R^1$ represents a hydrocarbon group which may have a substituent,
the hydrocarbon group has 1 to 30 carbon atoms,
the substituent is a group selected from a substituent group W,
the group selected from the substituent group W may be further substituted with a group selected from the substituent group W,
the substituent group W includes a halogen atom, a heteroaryl group, a cyano group, a hydroxyl group, a carboxyl group, a nitro group, an alkoxy group, an aryloxy group, a silyloxy group, a heterocyclic an oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, an alkyl or arylsulfinyl group, an alkyl or arylsulfonyl group, an acyl group, an aryloxycarbonyl group, an alkoxycarbonyl group, a carbamoyl group, an aryl or heterocyclic azo group, an imide group, a phosphino group, a phosphinyl group, a phosphinyloxy group, a phosphinylamino group, a phosphono group, a silyl group, a hydrazino group, an ureido group, and a boronic acid group, and
$R^2$ and $R^3$ each independently represent a hydrocarbon group substituted with a halogen atom, a cyano group, a nitro group, an acyl group, an alkyloxycarbonyl group, an aryloxycarbonyl group, an alkylsulfonyl group, an arylsulfonyl group, a dialkylsulfamoyl group, a dialkylamide group, or a heterocyclic group.

2. The production method according to claim 1,
wherein $R^2$ and $R^3$ each independently represent a fluorinated alkyl group having 1 to 10 carbon atoms.

3. The production method according to claim 1,
wherein the compound represented by Formula (1), the compound represented by Formula (2), and the oxidizing agent are mixed in a presence of a halogenated solvent.

4. The production method according to claim 2,
wherein the compound represented by Formula (1), the compound represented by Formula (2), and the oxidizing agent are mixed in a presence of a halogenated solvent.

5. The production method according to claim 1,
wherein $R^1$ represents a hydrocarbon group having a leaving group, and
the leaving group is a halogen atom, an alkylsulfonyloxy group which may have a group selected from the substituent group W, an arylsulfonyloxy group which may have a group selected from the substituent group W, an alkylsulfonyl group which may have a group selected from the substituent group W, an arylsulfonyl group which may have a group selected from the substituent group W, a methoxy group, an aryl ester group, or a nitro group.

6. The production method according to claim 2,
wherein $R^1$ represents a hydrocarbon group having a leaving group, and
the leaving group is a halogen atom, an alkylsulfonyloxy group which may have a group selected from the substituent group W, an arylsulfonyloxy group which may have a group selected from the substituent group W, an alkylsulfonyl group which may have a group selected from the substituent group W, an arylsulfonyl group which may have a group selected from the substituent group W, a methoxy group, an aryl ester group, or a nitro group.

7. The production method according to claim 3,
wherein $R^1$ represents a hydrocarbon group having a leaving group, and
the leaving group is a halogen atom, an alkylsulfonyloxy group which may have a group selected from the substituent group W, an arylsulfonyloxy group which may have a group selected from the substituent group W, an alkylsulfonyl group which may have a group selected from the substituent group W, an arylsulfonyl group which may have a group selected from the substituent group W, a methoxy group, an aryl ester group, or a nitro group.

8. The production method according to claim 5,
wherein the leaving group is a halogen atom.

9. The production method according to claim 1,
wherein the oxidizing agent is selected from the group consisting of an organic nitroxyl radical and an N-hydroxyl form of an organic nitroxyl radical.

10. The production method according to claim 2,
wherein the oxidizing agent is selected from the group consisting of an organic nitroxyl radical and an N-hydroxyl form of an organic nitroxyl radical.

11. The production method according to claim 3,
wherein the oxidizing agent is selected from the group consisting of an organic nitroxyl radical and an N-hydroxyl form of an organic nitroxyl radical.

12. The production method according to claim 4,
wherein the oxidizing agent is selected from the group consisting of an organic nitroxyl radical and an N-hydroxyl form of an organic nitroxyl radical.

13. The production method according to claim 1,
wherein the oxidizing agent is selected from the group consisting of a compound represented by Formula (4), a compound represented by Formula (5), and a compound represented by Formula (6),

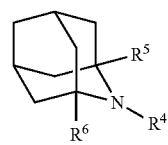
(4)

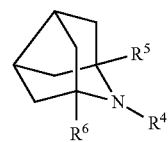
(5)

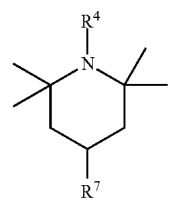
(6)

in the formulae, $R^4$ represents an oxyradical group or a hydroxyl group, $R^5$ and $R^6$ each independently represent a hydrogen atom or a methyl group, and $R^7$ represents a hydrogen atom, a halogen atom, a hydroxyl group, an acyloxy group, an alkoxy group, an alkoxycarbonyl group, an amino group, an oxo group, a sulfonyloxy group, an N-alkylcarbamoyloxy group, a carboxyl group, a cyano group, an isocyanato group, or an isothiocyanato group.

14. The production method according to claim 13,
further comprising mixing a reoxidizing agent.

15. The production method according to claim 14,
wherein the reoxidizing agent is a hypervalent iodine compound or an azodicarboxylic acid diester compound.

16. The production method according to claim 14,
wherein the reoxidizing agent is a hypervalent iodine compound.

17. The production method according to claim 1,
wherein the compound represented by Formula (1) is a compound represented by Formula (7), and
the hemiaminal compound represented by Formula (3) is a hemiaminal compound represented by Formula (8),

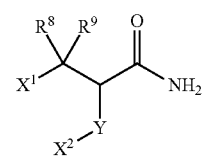
(7)

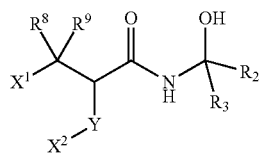
(8)

in Formulae, $R^8$ and $R^9$ each independently represent a hydrogen atom or a hydrocarbon group which may have a substituent, the hydrocarbon group has 1 to 30 carbon atoms, the substituent is a group selected from a substituent group W, the group selected from the substituent group W may be further substituted with a group selected from the substituent group W, the substituent group W includes a halogen atom, a heteroaryl group, a cyano group, a hydroxyl group, a carboxyl group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, an alkyl or arylsulfinyl group, an alkyl or arylsulfonyl group, an acyl group, an aryloxycarbonyl group, an alkoxycarbonyl group, a carbamoyl group, an aryl or heterocyclic azo group, an imide group, a phosphino group, a phosphinyl group, a phosphinyloxy group, a phosphinylamino group, a phosphono group, a silyl group, a hydrazino group, an ureido group, and a boronic acid group, Y represents a single bond or an aliphatic hydrocarbon group having 1 to 5 carbon atoms, which may have a heteroatom, $X^1$ and $X^2$ each independently represent a leaving group, the leaving group is a halogen atom, an alkylsulfonyloxy group which may have a group selected from the substituent group W, an arylsulfonyloxy group which may have a group selected from the substituent group W, an alkylsulfonyl group which may have a group selected from the substituent group W, an arylsulfonyl group which may have a group selected from the substituent group W, a methoxy group, an aryl ester group, or a nitro group, and $R^2$ and $R^3$ each independently represent a hydrocarbon group substituted with a halogen atom, a cyano group, a nitro group, an acyl group, an alkyloxycarbonyl group, an aryloxycarbonyl group, an alkylsulfonyl group, an arylsulfonyl group, a dialkylsulfamoyl group, a dialkylamide group, or a heterocyclic group.

18. A production method for a heterocyclic compound, comprising:
mixing the hemiaminal compound represented by Formula (8) obtained by the production method according to claim 17 with a base to obtain a heterocyclic compound represented by Formula (9),

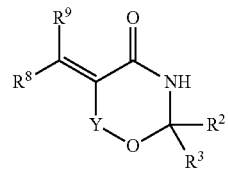

in the formula, $R^8$ and $R^9$ each independently represent a hydrogen atom or a hydrocarbon group which may have a substituent, the hydrocarbon group has 1 to 10 carbon atoms, the substituent is a group selected from a substituent group W, the group selected from the substituent group W may be further substituted with a group selected from the substituent group W, the substituent group W includes a halogen atom, a heteroaryl group, a cyano group, a hydroxyl group, a carboxyl group, a nitro group, an alkoxy group, an aryloxy group, a silyloxy group, a heterocyclic an oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, an alkyl or arylsulfinyl group, an alkyl or arylsulfonyl group, an acyl group, an aryloxycarbonyl group, an alkoxycarbonyl group, a carbamoyl group, an aryl or heterocyclic azo group, an imide group, a phosphino group, a phosphinyl group, a phosphinyloxy group, a phosphinylamino group, a phosphono group, a silyl group, a hydrazino group, an ureido group, and a boronic acid group, Y represents a single bond or an aliphatic hydrocarbon group having 1 to 5 carbon atoms, which may have a heteroatom, and $R^2$ and $R^3$ each independently represent a hydrocarbon group substituted with a halogen atom, a cyano group, a nitro group, an acyl group, an alkyloxycarbonyl group, an aryloxycarbonyl group, an alkylsulfonyl group, an arylsulfonyl group, a dialkylsulfamoyl group, a dialkylamide group, or a heterocyclic group.

* * * * *